United States Patent
Lechner et al.

(10) Patent No.: US 11,382,851 B2
(45) Date of Patent: Jul. 12, 2022

(54) HAIR DYE COMPOSITION CONTAINING AT LEAST ONE ORGANIC SILICON COMPOUND, A DIRECT DYE AND A FILM FORMING HYDROPHOBIC POLYMER

(71) Applicant: Henkel AG & Co. KGaA, Duesseldorf (DE)

(72) Inventors: Torsten Lechner, Langenfeld (DE); Marc Nowottny, Moenchengladbach (DE); Juergen Schoepgens, Schwalmtal (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 17/051,662

(22) PCT Filed: Mar. 21, 2019

(86) PCT No.: PCT/EP2019/057029
§ 371 (c)(1),
(2) Date: Oct. 29, 2020

(87) PCT Pub. No.: WO2019/214872
PCT Pub. Date: Nov. 14, 2019

(65) Prior Publication Data
US 2021/0186841 A1    Jun. 24, 2021

(30) Foreign Application Priority Data
May 7, 2018   (DE) .................... 10 2018 207 024.5

(51) Int. Cl.
*A61Q 5/10*   (2006.01)
*A61K 8/58*   (2006.01)
*A61K 8/81*   (2006.01)

(52) U.S. Cl.
CPC ............ *A61K 8/585* (2013.01); *A61K 8/8147* (2013.01); *A61K 8/8152* (2013.01); *A61K 8/8158* (2013.01); *A61Q 5/10* (2013.01); *A61K 2800/10* (2013.01); *A61K 2800/4324* (2013.01); *A61K 2800/884* (2013.01)

(58) Field of Classification Search
CPC .. A61Q 5/10; A61Q 5/065; A61K 2800/4324; A61K 2800/884; A61K 8/8152; A61K 8/25; A61K 8/8158; A61K 8/8147; A61K 8/585; A61K 2800/10; A61K 8/90; A61K 2800/432; A61K 2800/5424; A61K 8/895; A61K 8/89
USPC ............................................................ 8/405
See application file for complete search history.

(56) References Cited

U.S. PATENT DOCUMENTS

| | | | |
|---|---|---|---|
| 6,746,492 B2 | 6/2004 | Kawai et al. | |
| 7,806,941 B2 | 10/2010 | Brun et al. | |
| 2008/0184496 A1* | 8/2008 | Brun | A61K 8/585 8/435 |
| 2009/0151086 A1* | 6/2009 | Brun | A61K 8/8158 8/405 |
| 2010/0083446 A1* | 4/2010 | Brun | A61Q 5/004 8/405 |
| 2010/0154134 A1* | 6/2010 | Brun | C08K 5/0041 8/405 |
| 2010/0166844 A1* | 7/2010 | Mougin | A61Q 19/00 424/450 |
| 2014/0137342 A1* | 5/2014 | Guerin | A61Q 5/10 8/405 |

FOREIGN PATENT DOCUMENTS

| | | |
|---|---|---|
| DE | 10200185 A1 | 7/2002 |
| EP | 2168633 A2 | 3/2010 |

OTHER PUBLICATIONS

EPO, International Search Report issued in International Application No. PCT/EP2019/057029, dated May 17, 2019.

* cited by examiner

*Primary Examiner* — Eisa B Elhilo
(74) *Attorney, Agent, or Firm* — Lorenz & Kopf, LLP

(57) ABSTRACT

The subject of the present disclosure is a composition for coloring keratinous material, in particular human hair, containing in a cosmetic carrier
(a) at least one organic silicon compound selected from silanes having one, two or three silicon atoms, said organic silicon compound further comprising one or more basic chemical functions and one or more hydroxyl groups or hydrolysable groups per molecule,
(b) at least one direct dye; and
(c) at least one film-forming hydrophobic polymer.

13 Claims, No Drawings

HAIR DYE COMPOSITION CONTAINING AT LEAST ONE ORGANIC SILICON COMPOUND, A DIRECT DYE AND A FILM FORMING HYDROPHOBIC POLYMER

CROSS-REFERENCE TO RELATED APPLICATION

This application is a U.S. National-Stage entry under 35 U.S.C. § 371 based on International Application No. PCT/EP2019/057029, filed Mar. 21, 2019, which was published under PCT Article 21(2) and which claims priority to German Application No. 10 2018 207 024.5, filed May 7, 2018, which are all hereby incorporated in their entirety by reference.

TECHNICAL FIELD

The subject-matter of the present application is a composition for coloring keratinous material, in particular human hair, comprising, in a cosmetic carrier, (a) at least one specific organic silicon compound, (b) at least one direct dye and (c) at least one film-forming hydrophobic polymer.

Another subject of this notification is a kit-of-parts for dyeing keratinous material, in particular human hair, which comprises the agents (I), (II) and (III) separately packaged in three different containers. Here, agent (I) contains at least one organic silicon compound (a), agent (II) contains water, and agent (III) contains at least one direct-acting dye (b) and at least one film-forming, hydrophobic polymer (c).

A third object of the present disclosure is a process for dyeing keratinous material, which comprises the application of a pretreatment agent (V) and subsequently the application of a colorant (F). In this case, the pre-treatment agent (V) contains at least one specific organic silicon compound (a) in a water-containing cosmetic carrier.

The colorant (F) is exemplified by its content of at least one direct dye (b) and at least one film-forming, hydrophobic polymer (c).

BACKGROUND

The change in shape and color of keratin fibers, especially hair, is an important area of modern cosmetics. To change the hair color, the expert knows various coloring systems depending on coloring requirements. Oxidation dyes are usually used for permanent, intensive dyeing's with good fastness properties and good grey coverage. Such dyes usually contain oxidation dye precursors, so-called developer components and coupler components, which form the actual dyes with one another under the influence of oxidizing agents, such as hydrogen peroxide. Oxidation dyes are exemplified by very long-lasting dyeing results.

When direct dyes are used, ready-made dyes diffuse from the colorant into the hair fiber. Compared to oxidative hair dyeing, the dyeing's obtained with direct dyes have a shorter shelf life and quicker wash ability. Dyeing with direct dyes usually remain on the hair for a period of between about 5 and about 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, pigments can usually be removed again without leaving any residue by a few washes with detergents containing surfactants. Various products of this type are available on the market under the name hair mascara.

If the user wants particularly long-lasting dyeing's, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair.

EP 2168633 B1 deals with the task of producing long-lasting hair colorations using pigments. It teaches that by using a combination of pigment, organic silicon compound, hydrophobic polymer, and a solvent, it is possible to create colorations on hair that are particularly resistant to shampooing.

However, reworking the teaching of EP 2168633 B1 has shown that the dyeing's obtained in this way leave the hair with a poor feel. Due to their high insolubility, the pigments used in this gauge are present in particle form in the colorant. Trials have shown that these particles are deposited on the hair surface during the coloring process, leaving a rough and dull feeling on the hair surface. Appropriately colored strands of hair feel shaggy, are brittle and are difficult to comb.

The purpose of the present disclosure was to provide a dyeing system with fastness properties comparable to those of oxidative dyeing. Wash fastness properties should be outstanding, but the use of oxidation dye precursors normally used for this purpose should be avoided. A technology was sought that would make it possible to fix the coloring compounds known from the state of the art (such as direct dyes) to the hair in an extremely permanent way. However, the feel and combability of the hair should not be negatively affected. Even after coloring, the hair should still have a high gloss, be easy to comb and feel soft.

BRIEF SUMMARY

Compositions, multicomponent packaging units (kits-of-parts), and methods for dyeing keratinous material are provided herein. In an exemplary embodiment, the composition comprises, in a cosmetic carrier, at least one organic silicon compound selected from silanes having one, two or three silicon atoms, said organic silicon compound further comprising one or more basic chemical functions and one or more hydroxyl groups or hydrolysable groups per molecule, at least one direct dye, and at least one film-forming hydrophobic polymer.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, it has now been shown that the above-mentioned task can be achieved when keratinous materials, in particular hair, are dyed with an agent containing, in a cosmetic carrier, at least one specific organic silicon compound, at least one direct dye and at least one film-forming hydrophobic polymer.

A first object of the present disclosure is therefore an agent for coloring keratinous material, in particular human hair, containing in a cosmetic carrier (a) at least one organic silicon compound selected from silanes having one, two or three silicon atoms, said organic silicon compound further comprising one or more basic chemical functions and one or more hydroxyl groups or hydrolysable groups per molecule,
(b) at least one direct dye; and
(c) at least one film-forming hydrophobic polymer.

It was found that the combination of the present disclosure's organic silicon compound (a) and hydrophobic film-forming polymer (c) can fix the direct dyes (b) to the keratin fibers in a particularly permanent and long-lasting manner. Since the direct dyes have a higher solubility in water, they are not present in the form of particles but in dissolved form. For this reason, they do not weigh down the hair in an undesirable way but are deposited evenly on the surface of the keratin fibers or diffuse into the fibers.

Agent for Dyeing Keratinous Material

Keratinous material includes hair, skin, nails (such as fingernails and/or toenails). Wool, furs, and feathers also fall under the definition of keratinous material.

Preferably, keratinous material is understood to be human hair, human skin, and human nails, especially fingernails and toenails. Keratinous material is understood to be human hair.

The compositions as contemplated herein contain the compounds (a), (b) and (c) essential to the present disclosure in a cosmetic carrier, preferably in a suitable aqueous or aqueous-alcoholic carrier. For hair coloration, such carriers are, for example, creams, emulsions, gels, or surfactant-containing foaming solutions, such as shampoos, foam aerosols, foam formulations or other preparations suitable for application to the hair.

The cosmetic carrier preferably contains water, which means that the carrier contains at least about 2% by weight of water based on its weight. Preferably, the water content is above about 5 wt. %, further preferably above about 10 wt. % still further preferably above about 15 wt. %. The cosmetic carrier can also be aqueous alcoholic. [0206] Aqueous/alcoholic solutions in the context of the present disclosure are aqueous solutions containing from about 2 to about 70% by weight of a $C_1$-$C_4$ alcohol, more particularly ethanol or isopropanol. The agents as contemplated herein may additionally contain other organic solvents, such as methoxy butanol, benzyl alcohol, ethyl diglycol or 1,2-propylene glycol. Preferred are all water-soluble organic solvents.

The cosmetic carrier can also be aqueous alcoholic. During this dyeing process, the direct dyes are deposited in a particularly homogeneous and smooth film on the surface of the keratin material or diffuse into the keratin fibers. The film is formed in situ by oligomerization or polymerization of the organic silicon compound(s) and by the interaction of direct dye and organic silicon compound with the hydrophobic, film-forming polymer.

Organic Silicon Compounds

As a first present disclosure-essential ingredient (a), the employing present disclosure contain at least one organic silicon compound selected from silanes having one, two or three silicon atoms, said organic silicon compound further comprising one or more basic chemical functions and one or more hydroxyl groups or hydrolysable groups per molecule.

Organic silicon compounds, alternatively called organo-silicon compounds, are compounds which either have a direct silicon-carbon bond (Si—C) or in which the carbon is bonded to the silicon atom via an oxygen, nitrogen, or sulfur atom. The organic silicon compounds as contemplated herein are compounds containing one to three silicon atoms. Organic silicon compounds preferably contain one or two silicon atoms.

The organic silicon compounds (a) contain at least one basic group. This basic group can be, for example, an amino group, an alkylamino group or a dialkylamino group, which is preferably connected to a silicon atom via a linker. The basic group is preferably an amino group, a $C_1$-$C_6$ alkylamino group or a di($C_1$-$C_6$)alkylamino group.

Furthermore, the organic silicon compounds include at least one hydroxy group or a hydrolysable group. The hydrolysable group(s) is (are) preferably a $C_1$-$C_6$ alkoxy group, especially an ethoxy group or a methoxy group. It is preferred when the hydrolysable group is directly bonded to the silicon atom. For example, if the hydrolysable group is an ethoxy group, the organic silicon compound preferably contains a structural unit R'R''R'''Si—O—CH2-CH3. The residues R', R'' and R''' represent the three remaining free valences of the silicon atom.

Particularly good results could be obtained if the means as contemplated herein contained at least one organic silicon compound (a) of formula (I) and/or (II), In another preferred embodiment, an agent as contemplated herein contains at least one organic silicon compound (a) of formula (I) and/or (II).

$$R_1R_2N\text{-}L\text{-}Si(OR_3)_a(R_4)_b \qquad (I),$$

where
$R_1$, $R_2$ independently represent a hydrogen atom or a $C_1$-$C_6$ alkyl group,
L is a linear or branched divalent $C_1$-$C_{20}$ alkylene group,
R3 represents a hydrogen atom or a $C_1$-C alkyl group
R4 represents a C1-C6 alkyl group
a, stands for an integer from 1 to 3, and
b stands for the integer 3-a,

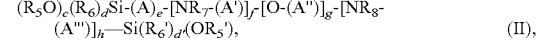

$$(R_5O)_c(R_6)_d Si\text{-}(A)_e\text{-}[NR_7\text{-}(A')]_f\text{-}[O\text{-}(A'')]_g\text{-}[NR_8\text{-}(A''')]_h\text{—}Si(R_6')_{d'}(OR_5'), \qquad (II),$$

where
R5, R5', R5" independently represent a hydrogen atom or a $C_1$-$C_6$ alkyl group,
R6, R6' and R6" independently represent a $C_1$-$C_6$ alkyl group,
A, A', A", independently of one another represent a linear or branched divalent $C_1$-$C_{20}$ alkylene group
$R_7$ and $R_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III)

$$\text{-}(A'''')\text{-}Si(R_6'')_{d''}(OR_5'')_{c''} \qquad (III),$$

c, stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
provided that at least one of e, f, g, and h is different from 0.

The substituents $R_1$, $R_2$, $R_3$, $R_4$, $R_5$, $R_5'$, $R_5''$, $R_6$, $R_6'$, $R_6''$, $R_7$, $R_8$, L, A', A'' and A'''' in the compounds of formula (I) and (II) are explained below as examples: Examples of a $C_1$-$C_6$ alkyl group are the groups methyl, ethyl, propyl, isopropyl, n-butyl, s-butyl, and t-butyl, n-pentyl and n-hexyl. Propyl, ethyl, and methyl are preferred alkyl radicals. Examples of a $C_2$-$C_6$ alkenyl group are vinyl, allyl, but-2-enyl, but-3-enyl and isobutenyl, preferred $C_2$-$C_6$ alkenyl radicals are vinyl and allyl. Preferred examples of a hydroxy $C_1$-$C_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino $C_1$-$C_6$ alkyl group are the aminomethyl group, the 2-aminoethyl group, the 3-aminopropyl group. The 2-aminoethyl group is particularly preferred. Examples of a linear divalent $C_1$-$C_{20}$ alkylene group include the methylene group (—$CH_2$—), the ethylene group (—$CH_2$—$CH_2$—), the propylene group (—$CH_2$—$CH_2$—$CH_2$—) and the butylene group (—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched divalent $C_3$-$C_{20}$ alkylene groups are (—$CH_2$—CH($CH_3$)—) and (—$CH_2$—CH($CH_3$)—$CH_2$—).

In the organic silicon compounds of the formula (I)

the radicals $R_1$ and $R_2$ independently of one another represent a hydrogen atom or a $C_1$-$C_6$ alkyl group. In particular, the radicals $R_1$ and $R_2$ both represent a hydrogen atom.

In the middle part of the organic silicon compound is the structural unit or the linker -L-, which stands for a linear or branched, divalent $C_1$-$C_2$ alkylene group.

Preferably -L- stands for a linear, divalent $C_1$-$C_{20}$ alkylene group. Further preferably -L- stands for a linear divalent $C_1$-$C_6$ alkylene group. Particularly preferred -L stands for a methylene group ($CH_2$—), an ethylene group (—$CH_2$—$CH_2$—), propylene group (—$CH_2$—$CH_2$—$CH_2$—) or butylene (—$CH_2$—$CH_2$—$CH_2$—$CH_2$—). L stands for a propylene group (—$CH_2$—$CH_2$—$CH_2$—)

In another preferred embodiment, an agent as contemplated herein contains (a) at least one organic silicon compound of formula (I),

where $R_1$, $R_2$ both represent a hydrogen atom, and

L represents a linear, divalent $C_1$-$C_6$-alkylene group, preferably a propylene group (—$CH_2$—$CH_2$—$CH_2$—) or an ethylene group (—$CH_2$—$CH_2$—).

The organic silicon compounds of formula (I)

carry the silicon-containing grouping —Si($OR_3$)$_a$($R_4$)$_b$ at one end.

In the terminal structural unit —Si($OR_3$)$_a$($R_4$)$_b$, $R_3$ is hydrogen or $C_1$-$C_6$ alkyl group, and $R_4$ is $C_1$-$C_6$ alkyl group. $R_3$ and $R_4$ independently of each other represent a methyl group or an ethyl group.

Here a stands for an integer from 1 to 3, and b stands for the integer 3-a. If a stands for the number 3, then b is equal to 0. If a stands for the number 2, then b is equal to 1. If a stands for the number 1, then b is equal to 2.

Dyes with the best wash fastness values could be obtained if the pretreatment agent contains at least one organic silicon compound corresponding to formula (I): in which $R_3$, $R_4$ independently of one another represent a methyl group or an ethyl group.

Furthermore, dyeing's with the best wash fastness properties could be obtained if the agent as contemplated herein contains at least one organic silicon compound of formula (I) in which the radical a represents the number 3. In this case the rest b stands for the number 0.

In a further preferred embodiment, an agent as contemplated herein contains (a) at least one organic silicon compound of formula (I), where $R_3$ represents a hydrogen atom, a methyl group, or an ethyl group, $R_4$ represents a methyl group or an ethyl group, a stands for the number 3 and b stands for the number 0.

In another particularly preferred embodiment, an agent as contemplated herein contains (a) at least one organic silicon compound of formula (I), where $R_3$, $R_4$ independently of one another represent a methyl group or an ethyl group and a stands for the number 3 and b stands for the number 0.

Organic silicon compounds of the formula (I) which are particularly suitable for solving the problem as contemplated herein are (3-Aminopropyl)triethoxysilane

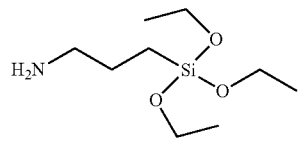

(3-Aminopropyl)trimethoxysilane

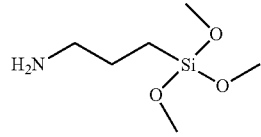

1-(3-Aminopropyl)silantriol

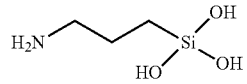

(2-Aminoethyl)triethoxysilane

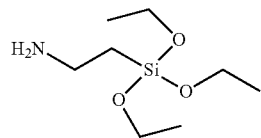

(2-Aminoethyl)trimethoxysilane

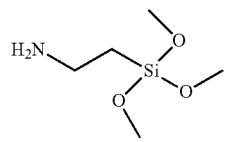

1-(2-Aminoethyl)silantriol

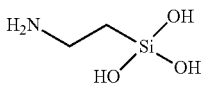

(3-Dimethylaminopropyl)triethoxysilane

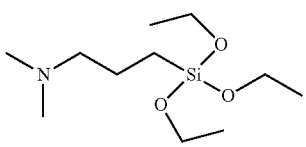 [SMILES: CCO[Si](CCCN(C)C)(OCC)OCC]

(3-Dimethylaminopropyl)trimethoxysilane

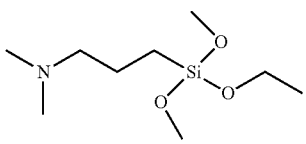

1-(3-Dimethylaminopropyl)silantriol

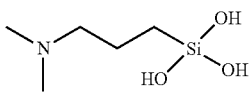

(2-Dimethylaminoethyl)triethoxysilane.

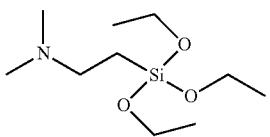

(2-Dimethylaminoethyl)trimethoxysilane and/or

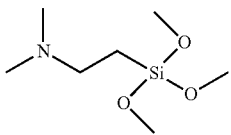

1-(2-Dimethylaminoethyl)silantriol

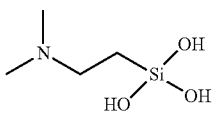

In another preferred embodiment, an agent as contemplated herein contains (a) at least one organic silicon compound of formula (I) selected from the group including
(3-Aminopropyl)triethoxysilan
(3-Aminopropyl)trimethoxysilane
1-(3-Aminopropyl)silantriol
(2-Aminoethyl)triethoxysilan
(2-Aminoethyl)trimethoxysilane
1-(2-Aminoethyl)silantriol
(3-Dimethylaminopropyl)triethoxysilan
(3-Dimethylaminopropyl)trimethoxysilane
1-(3-Dimethylaminopropyl)silantriol
(2-Dimethylaminoethyl)triethoxysilan.
(2-Dimethylaminoethyl)trimethoxysilane and/or
1-(2-Dimethylaminoethyl)silantriol.

The organic silicon compound of formula (I) is commercially available. (3-Aminopropyl)trimethoxysilane, for example, can be purchased from Sigma-Aldrich. Also (3-Aminopropyl)triethoxysilane is commercially available from Sigma-Aldrich.

In a further version, the present disclosure contains at least one organic silicon compound of formula (II)

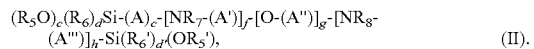

The organosilicon compounds of formula (II) as contemplated herein each carry the silicon-containing groups $(R_5O)_c(R_6)_dSi-$ and $-Si(R_6')_{d'}(OR_5')_{c'}$ at both ends.

In the central part of the molecule of formula (II) there are the groups $-(A)_e-$ and $-[NR_7-(A')]_f-$ and $-[O-(A'')]_g-$ and $-[NR_8-(A''')]_h-$. Here, each of the radicals e, f, g, and h can independently of one another stand for the number 0 or 1, with the proviso that at least one of the radicals e, f, g, and h is different from 0. In other words, an organic silicon compound of formula (II) as contemplated herein contains at least one grouping from the group including $-(A)-$ and $-[NR_7-(A')]-$ and $-[O-(A'')]-$ and $-[NR_8-(A''')]-$.

In the two terminal structural units $(R_5O)_c(R_6)_dSi-$ and $-Si(R_6')_{d'}(OR_5')_{c'}$, the radicals R5, R5', R5" independently of one another represent a hydrogen atom or a $C_1-C_6$ alkyl group. The radicals R6, R6' and R6" independently represent a $C_1-C_6$ alkyl group.

Here a stands for an integer from 1 to 3, and d stands for the integer 3-c. If c stands for the number 3, then d is equal to 0. If c stands for the number 2, then d is equal to 1. If c stands for the number 1, then d is equal to 2.

Analogously c' stands for a whole number from 1 to 3, and d' stands for the whole number 3-c'. If c' stands for the number 3, then d' is 0. If c' stands for the number 2, then d' is 1. If c' stands for the number 1, then d' is 2.

Dyeing's with the best wash fastness values could be obtained if the residues c and c' both stand for the number 3. In this case d and d' both stand for the number 0.

In another preferred embodiment, an agent as contemplated herein contains (a) at least one organic silicon compound of formula (II),

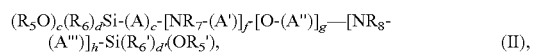

where
R5 and R5' independently represent a methyl group or an ethyl group,
c and c' both stand for the number 3 and
d and d' both stand for the number 0.

If c and c' are both the number 3 and d and d' are both the number 0, the organic silicon compound of the present disclosure corresponds to formula (IIa)

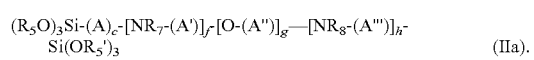

The radicals e, f, g, and h can independently stand for the number 0 or 1, whereby at least one radical from e, f, g, and h is different from zero. The abbreviations e, f, g and h thus define which of the groupings $-(A)_e-$ and $-[NR_7-(A')]_f-$ and —[O-(A")]$_g$- and —[NR$_8$-(A''')]$_h$- are located in the middle part of the organic silicon compound of formula (II).

In this context, the presence of certain groupings has proved to be particularly beneficial in terms of increasing washability. Particularly good results were obtained when at least two of the residues e, f, g, and h stand for the number 1. Especially preferred e and f both stand for the number 1. Furthermore, g and h both stand for the number 0.

If e and f both stand for the number 1 and g and h both stand for the number 0, the organic silicon compound as contemplated herein corresponds to formula (IIb)

$$(R_5O)_e(R_6)_d Si-(A)-[NR_7-(A')]-Si(R_6')_d(OR_4')_{e'} \qquad (IIb).$$

The radicals A, A', A", A''' and A"" independently represent a linear or branched divalent $C_1$-$C_{20}$ alkylene group. Preferably the radicals A, A', A", A''' and A"" independently of one another represent a linear, divalent $C_1$-$C_{20}$ alkylene group. Further preferably the radicals A, A', A", A''' and A"" independently represent a linear divalent $C_1$-$C_6$ alkylene group. In particular, the radicals A, A', A", A''' and A"" independently of one another represent a methylene group (—CH$_2$—), an ethylene group (—CH$_2$—CH$_2$—), a propylene group (—CH$_2$—CH$_2$—CH$_2$—) or a butylene group (—CH$_2$—CH$_2$—CH$_2$—CH$_2$—). In particular, the residues A, A', A", A''' and A"" stand for a propylene group (—CH$_2$—CH$_2$—CH$_2$—).

If the radical f represents the number 1, then the organic silicon compound of formula (II) as contemplated herein contains a structural grouping —[NR$_7$-(A')]-.

If the radical f represents the number 1, then the organic silicon compound of formula (II) as contemplated herein contains a structural grouping —[NR$_8$-(A''')]-.

Wherein R$_7$ and R$_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of the formula (III)

$$-(A'''')-Si(R_6'')_{d''}(OR_5'')_{e''} \qquad (III).$$

Very preferably the radicals R7 and R8 independently of one another represent a hydrogen atom, a methyl group, a 2-hydroxyethyl group, a 2-alkenyl group, a 2-aminoethyl group or a grouping of the formula (III).

If the radical f represents the number 1 and the radical h represents the number 0, the organic silicon compound as contemplated herein contains the grouping [NR$_7$-(A')] but not the grouping —[NR$_8$-(A''')]. If the radical R$_7$ now stands for a grouping of the formula (III), the pretreatment agents (A) contains an organic silicon compound with 3 reactive silane groups.

In another preferred embodiment, an agent as contemplated herein contains (a) at least one organic silicon compound of formula (II), $$(R_5O)_e(R_6)_d Si-(A)_c-[NR_7-(A')]_f-[O-(A'')]_g-[NR_8-(A''')]_h-Si(R_6')_d(OR_5')_{e'} \qquad (II),$$

where
e and f both stand for the number 1,
g and h both stand for the number 0,
A and A' independently represent a linear, divalent $C_1$-$C_6$ alkylene group and
R7 represents a hydrogen atom, a methyl group, a 2-hydroxyethyl group, a 2-alkenyl group, a 2-aminoethyl group or a group of formula (III).

In a further preferred embodiment, an agent as contemplated herein contains (a) at least one organic silicon compound of formula (II), where
e and f both stand for the number 1,
g and h both stand for the number 0,
A and A' independently of one another represent a methylene group (—CH$_2$—), an ethylene group (—CH$_2$—CH$_2$—) or a propylene group (—CH$_2$—CH$_2$—CH$_2$—), and
R7 represents a hydrogen atom, a methyl group, a 2-hydroxyethyl group, a 2-alkenyl group, a 2-aminoethyl group or a group of formula (III).

Organic silicon compounds of the formula (II) which are particularly suitable for solving the problem as contemplated herein are 3-(Trimethoxysilyl)-N-[3-(trimethoxysilyl)propyl]-1-propanamine

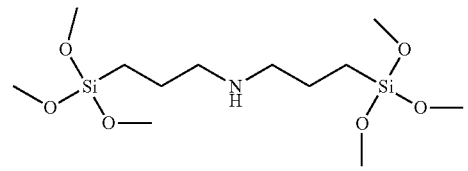

3-(Triethoxysilyl)-N-[3-(triethoxysilyl)propyl]-1-propanamine

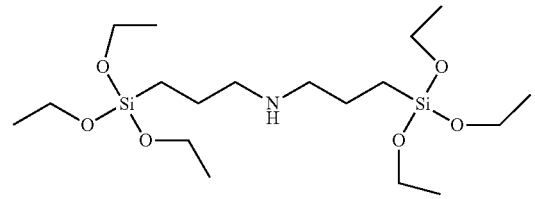 [SMILES: CCO[Si](CCCNCCC[Si](OCC)(OCC)OCC)(OCC)OCC]

N-Methyl-3-(triethoxysilyl)-N-[3-(triethoxysilyl)propyl]-1-propanamine

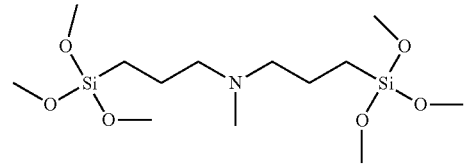

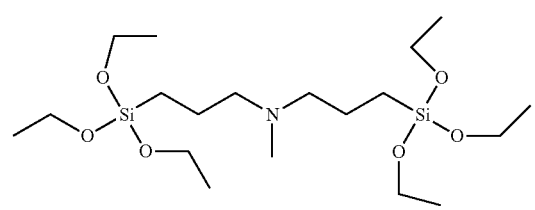 [SMILES: CCO[Si](CCCN(C)CCC[Si](OCC)(OCC)OCC)(OCC)OCC]

2-[Bis[3-(trimethoxysilyl)_propyl]amino]-ethanol

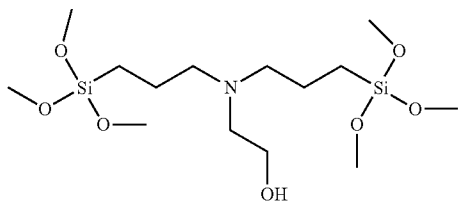

2-[Bis[3-(triethoxysilyl)propyl]amino]ethanol

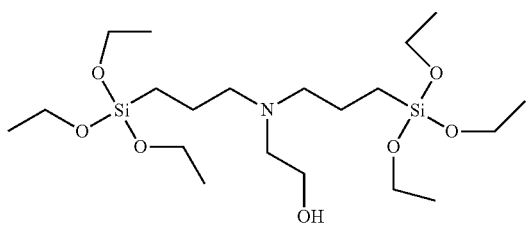 [SMILES: CCO[Si](CCCN(CCO)CCC[Si](OCC)(OCC)OCC)(OCC)OCC]

3-(Trimethoxysilyl)-N,N-bis[3-(trimethoxysilyl)propyl]-1-propanamine

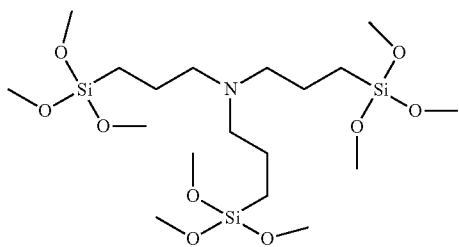

3-(Triethoxysilyl)-N,N-bis[3-(triethoxysilyl)propyl]-1-propanamine

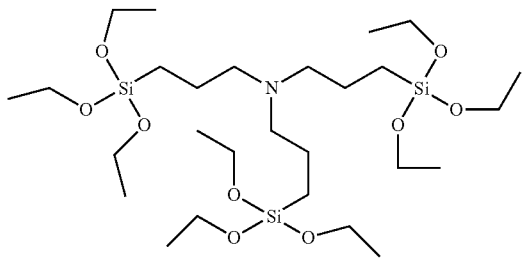 [SMILES: CCO[Si](CCCN(CCC[Si](OCC)(OCC)OCC)CCC[Si](OCC)(OCC)OCC)(OCC)OCC]

N1,N1-Bis[3-(trimethoxysilyl)propyl]-1,2-ethanediamine,

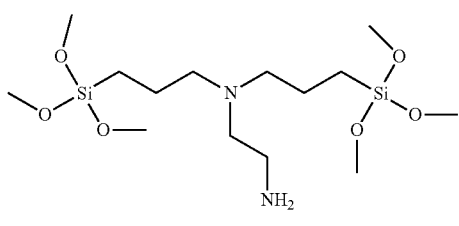

N1,N1-Bis[3-(triethoxysilyl)propyl]-1,2-ethanediamine,

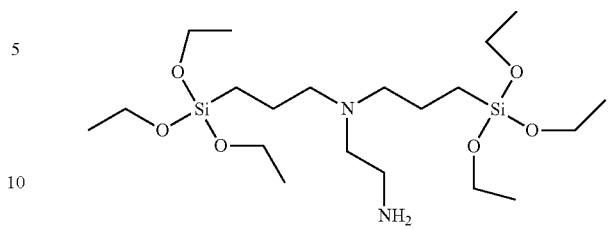

N,N-Bis[3-(trimethoxysilyl)propyl]-2-propen-1-amine

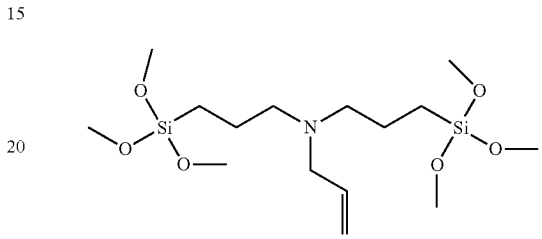

N,N-Bis[3-(triethoxysilyl)propyl]-2-propen-1-amine

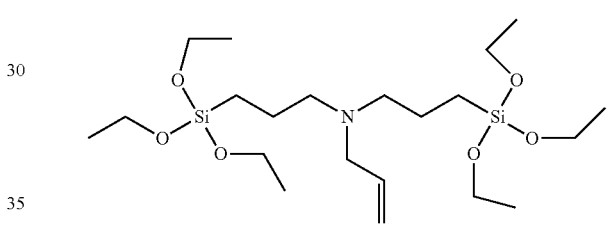

The organic silicon compounds of formula (II) are commercially available.
Bis(trimethoxysilylpropyl)amines with the CAS number 82985-35-1 can be purchased from Sigma-Aldrich.
Bis[3-(triethoxysilyl)propyl]amines with the CAS number 13497-18-2 can be purchased from Sigma-Aldrich, for example.
N-Methyl-3-(trimethoxysilyl)-N-[3-(trimethoxysilyl)propyl]-1-propanamine is alternatively referred to as Bis(3-trimethoxysilylpropyl)-N-methylamine and can be purchased commercially from Sigma-Aldrich or Fluorochem.
3-(Triethoxysilyl)-N,N-bis[3-(triethoxysilyl)propyl]-1-propanamine with the CAS number 18784-74-2 can be purchased for example from Fluorochem or Sigma-Aldrich.

In another preferred embodiment, an agent as contemplated herein contains (a) at least one organic silicon compound of formula (II) selected from the group including
3-(Trimethoxysilyl)-N-[3-(trimethoxysilyl)propyl]-1-propanamine
3-(Triethoxysilyl)-N-[3-(triethoxysilyl)propyl]-1-propanamine
N-Methyl-3-(trimethoxysilyl)-N-[3-(trimethoxysilyl)propyl]-1-propanamine
N-Methyl-3-(triethoxysilyl)-N-[3-(triethoxysilyl)propyl]-1-propanamine
2-[Bis[3-(trimethoxysilyl)propyl]amino]-ethanol
2-[Bis[3-(triethoxysilyl)propyl]amino]ethanol
3-(Trimethoxysilyl)-N,N-bis[3-(trimethoxysilyl)propyl]-1-propanamine 3-(Triethoxysilyl)-N,N-bis[3-(triethoxysilyl)propyl]-1-propanamine
N1,N1-Bis[3-(trimethoxysilyl)propyl]-1,2-ethanediamine,
N1,N1-Bis[3-(triethoxysilyl)propyl]-1,2-ethanediamine,
N,N-Bis[3-(trimethoxysilyl)propyl]-2-propen-1-amine and/or
N,N-Bis[3-(triethoxysilyl)propyl]-2-propen-1-amine.

The organic silicon compounds of formula (I) and (II) are reactive compounds. In this context, it has been found to be preferred if the employing the present disclosure contains—based on its total weight—one or more organic silicon compounds (a) in a total amount of from about 0.1 to about 20.0% by weight, preferably from about 0.2 to about 15.0% by weight and particularly preferably from about 0.2 to about 2.0% by weight.

In this context, it has turned out to be particularly preferred if the agent of the present disclosure contains—based on its total weight—one or more organic silicon compounds (a) of the formula (I) and/or (II) in a total amount of from about 0.1 to about 20.0% by weight, preferably from about 0.2 to about 15.0% by weight and particularly preferably from about 0.2 to about 2.0% by weight.

It has been shown to be particularly suitable to use at least one organic silicon compound of formula (I) in the present disclosure.

In another preferred embodiment, an agent as contemplated herein contains (a) at least one organic silicon compound of formula (I).

Direct Dyes

As a second essential ingredient (b), the means as contemplated herein contain at least direct dye.

Direct dyes are dyes that are applied directly to the hair and do not require an oxidative process to form the color. Direct dyes are usually nitro phenylene diamines, nitroaminophenols, azo dyes, anthraquinones, triarylmethane dyes or indophenols.

Direct dyes can be divided into anionic, cationic, and nonionic direct dyes.

The direct dyes within the meaning of the present disclosure have a solubility in water (about 760 mmHg) at about 25° C. of more than about 0.5 g/L and are therefore not to be regarded as pigments.

Preferably, the direct dyes within the meaning of the present disclosure have a solubility in water (about 760 mmHg) at about 25° C. of more than about 1.0 g/L. In particular, the direct dyes within the meaning of the present disclosure have a solubility in water (about 760 mmHg) at about 25° C. of more than about 1.5 g/L.

In the context of another version, a composition for coloring keratinous material, in particular human hair, containing, in a cosmetic carrier
(a) at least one organic silicon compound selected from silanes having one, two or three silicon atoms, said organic silicon compound further comprising one or more basic chemical functions and one or more hydroxyl groups or hydrolysable groups per molecule,
(b) at least one direct dye which has a solubility in water (about 760 mmHg) at about 25° C. of more than about 0.5 g/L, preferably more than about 1.0 g/L, particularly preferably more than about 1.5 g/L, and
(c) at least one film-forming hydrophobic polymer.

Suitable cationic direct dyes include Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76.

As non-ionic direct dyes, non-ionic nitro and quinone dyes and neutral azo dyes can be used. Suitable non-ionic direct dyestuffs are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol.

In the course of the work leading to this present disclosure, it has been found that dyes with particularly high color intensity can be produced, with agents containing (b) at least one anionic direct dye.

In an explicitly particularly preferred embodiment, an agent as contemplated herein contains (b) at least one anionic direct dye.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—COO$^-$, —SO$_3^-$ present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Inventive acid dyes can also be used in the form of their sodium salts and/or their potassium salts.

The acid dyes within the meaning of the present disclosure have a solubility in water (about 760 mmHg) at about 25° C. of more than about 0.5 g/L and are therefore not to be regarded as pigments. Preferably the acid dyes within the meaning of the present disclosure have a solubility in water (about 760 mmHg) at about 25° C. of more than about 1.0 g/L.

The alkaline earth salts (such as calcium salts and magnesium salts) or aluminum salts of acid dyes often have a lower solubility than the corresponding alkali salts. If the solubility of these salts is below about 0.5 g/L (about 25° C., about 760 mmHg), they are not covered by the present disclosure.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In the context of an embodiment, an agent for coloring keratinous material is thus preferred, which
(b) contains at least one anionic direct dye selected from the group including nitrophenylenediamines, nitroaminophenols, azo dyes, anthraquinone dyes, triarylmethane dyes, xanthene dyes, rhodamine dyes, oxazine dyes and/or indophenol dyes, wherein the dyes from the aforementioned group each have at least one carboxylic acid group (—COOH), a sodium carboxylate group (—COONa), a potassium carboxylate group (—COOK), a sulphonic acid group (—SO$_3$H), a sodium sulphonate group (—SO$_3$Na) and/or a potassium sulphonate group (—SO$_3$K).

For example, one or more compounds from the following group can be selected as particularly well suited acid dyes: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; no sodium salt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Red 46, Real Red D, FD&C Red No. 2, Food Red 9, Naphthol Red S), Acid Red 33 (Red 33, Fuchsia Red, D&C Red 33, CI 17200), Acid Red 35 (CI C.I.18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI 27290), Acid Red 87 (Eosin, CI 45380), Acid Red 92 (COLIPA no C53, CI 45410), Acid Red 95 (CI 45425, Erythtosine, Simacid Erythrosine Y), Acid Red 184 (CI 15685), Acid Red 195, Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent blue AE, Amido blue AE, Erioglaucine A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant acid green BS, C.I. 44090, Acid Brilliant Green BS, E 142), Acid Black 1 (Black no 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. about 0.1 g of the anionic direct dye is placed in a beaker. A stir-fish is added. Then add about 100 ml of water. This mixture is heated to about 25° C. on a magnetic stirrer while stirring. It is stirred for about 60 minutes. The aqueous mixture is then visually assessed. If there are still undissolved residues, the amount of water is increased—for example in steps of about 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If about 0.1 g of the anionic direct dye dissolves in about 100 ml water at about 25° C., the solubility of the dye is about 1.0 g/L.

Acid Yellow 1 is called 8-hydroxy-5,7-dinitro-2-naphthalenesulfonic acid disodium salt and has a solubility in water of at least about 40 g/L (about 25° C.).

Acid Yellow 3 is a mixture of the sodium salts of mono- and sisulfonic acids of 2-(2-quinolyl)-1H-indene-1,3(2H)-dione and has a water solubility of about 20 g/L (about 25° C.).

Acid Yellow 9 is the disodium salt of 8-hydroxy-5,7-dinitro-2-naphthalenesulfonic acid, its solubility in water is above about 40 g/L (about 25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at about 25° C.

Acid Orange 7 is the sodium salt of 4-[(2-hydroxy-1-naphthyl)azo]benzene sulphonate. Its water solubility is more than about 7 g/L (about 25° C.).

Acid Red 18 is the trinatirum salt of 7-hydroxy-8-[(E)-(4-sulfonato-1-naphthyl)-diazenyl)]-1,3-naphthalene disulfonate and has a very high-water solubility of more than about 20% by weight.

Acid Red 33 is the disodium salt of 5-amino-4-hydroxy-3-(phenylazo)-naphthalene-2,7-disulphonate, its solubility in water is about 2.5 g/L (about 25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than about 10 g/L (about 25° C.).

Acid Blue 9 is the disodium salt of 2-({4-[N-ethyl(3-sulfonatobenzyl]amino]phenyl}{4-[(N-ethyl(3-sulfonatobenzyl)imino]-2,5-cyclohexadien-1-ylidene}methyl)-benzenesulfonate and has a solubility in water of more than about 20% by weight (about 25° C.).

A particularly preferred employing present disclosure contains (b) at least one anionic direct dye from the group including Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct dyestuff(s), in the anionic direct dyestuff(s), may be used in varying quantities in the employing the present disclosure, depending on the desired color intensity. Particularly good results could be obtained if the agent as contemplated herein—based on its total weight—contains one or more direct dyes (b) in a total amount of from about 0.01 to about 10.0 wt. %, preferably from about 0.1 to about 8.0 wt. %, further preferably from about 0.2 to about 6.0 wt. % and very particularly preferably from about 0.5 to about 4.5 wt. %.

In a further preferred embodiment, an agent as contemplated herein contains—based on its total weight—one or more direct dyes (b) in a total amount of from about 0.01 to about 10.0% by weight, preferably from about 0.1 to about 8.0% by weight, more preferably from about 0.2 to about 6.0% by weight and very particularly preferably from about 0.5 to about 4.5% by weight.

In a further preferred version, an agent as contemplated herein contains—based on its total weight—one or more anionic direct-acting dyes (b) in a total amount of from about 0.01 to about 10.0% by weight, preferably from about 0.1 to about 8.0% by weight, more preferably from about 0.2 to about 6.0% by weight and very particularly preferably from about 0.5 to about 4.5% by weight.

Film Forming, Hydrophobic Polymer

As the third constituent essential to the present disclosure (c), the means as contemplated herein contain at least one film-forming, hydrophobic polymer.

Polymers are macromolecules with a molecular weight of at least about 1000 g/mol, preferably of at least about 2500 g/mol, particularly preferably of at least about 5000 g/mol, which includes identical, repeating organic units. The polymers of the present disclosure may be synthetically produced polymers which are manufactured by polymerization of one type of monomer or by polymerization of different types of monomer which are structurally different from each other. If the polymer is produced by polymerizing a type of monomer, it is called a homo-polymer. If structurally different monomer types are used in polymerization, the resulting polymer is called a copolymer.

The maximum molecular weight of the polymer depends on the degree of polymerization (number of polymerized monomers) and the batch size and is determined by the polymerization method. For the purposes of the present disclosure, it is preferred that the maximum molecular weight of the film-forming hydrophobic polymer (c) is not more than about $10^7$ g/mol, preferably not more than about $10^6$ g/mol and particularly preferably not more than about $10^5$ g/mol.

A hydrophobic polymer is a polymer that has a solubility in water at about 25° C. (about 760 mmHg) of less than about 1% by weight.

The water solubility of the film-forming, hydrophobic polymer can be determined in the following way, for example. about 1.0 g of the polymer is placed in a beaker. Make up to about 100 g with water. A stir-fish is added, and the mixture is heated to about 25° C. on a magnetic stirrer while stirring. It is stirred for about 60 minutes. The aqueous mixture is then visually assessed. If the polymer-water mixture cannot be assessed visually due to a high turbidity of the mixture, the mixture is filtered. If a proportion of undissolved polymer remains on the filter paper, the solubility of the polymer is less than about 1% by weight.

As contemplated herein, a film-forming polymer is a polymer which can form a film on a substrate, for example on a keratinic material or a keratinic fiber. The formation of a film can be demonstrated, for example, by looking at the keratin material treated with the polymer under a microscope.

These include acrylic acid-type polymers, polyurethanes, polyesters, polyamides, polyureas, cellulose polymers, nitrocellulose polymers, silicone polymers, acrylamide-type polymers, and polyisoprenes.

Particularly well suited film-forming, hydrophobic polymers are, for example, polymers from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

In a further preferred embodiment, an agent as contemplated herein contains at least one film-forming hydrophobic polymer (c) selected from the group including copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

The film-forming hydrophobic polymers, which are selected from the group of synthetic polymers, polymers obtainable by radical polymerization or natural polymers, have proved to be particularly suitable for solving the problem as contemplated herein.

Other particularly well suited film-forming hydrophobic polymers can be selected from the homopolymers or copolymers of olefins, such as cycloolefins, butadiene, isoprene or styrene, vinyl ethers, vinylamides, the esters or amides of (meth)acrylic acid with at least one $C_1$-$C_{20}$ alkyl group, an aryl group or a C2-C10 hydroxyalkyl group.

Other film-forming hydrophobic polymers may be selected from the homo- or copolymers of isooctyl (meth)acrylate; isonononyl (meth)acrylate; 2-ethylhexyl (meth)acrylate; lauryl (meth)acrylate; isopentyl (meth)acrylate; n-butyl (meth)acrylate); isobutyl (meth)acrylate; ethyl (meth)acrylate; methyl (meth)acrylate; tert-butyl (meth)acrylate; stearyl (meth)acrylate; hydroxyethyl (meth)acrylate; 2-hydroxypropyl (meth)acrylate; 3-hydroxypropyl (meth)acrylate and/or mixtures thereof.

Other film-forming hydrophobic polymers may be selected from the homo- or copolymers of (meth)acrylamide; N-alkyl-(meth)acrylamides, in particular those with C2-C18 alkyl groups, such as N-ethyl-acrylamide, N-tert-butyl-acrylamide, le N-octyl-crylamide; N-di(C1-C4)alkyl-(meth)acrylamide.

Other preferred anionic copolymers are, for example, copolymers of acrylic acid, methacrylic acid or their $C_1$-$C_6$ alkyl esters, as they are marketed under the INCI Declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Some of the most preferred polymers on the market are Aculyn® 22 (acrylates/steareth-20 methacrylate copolymer), Aculyn® 28 (acrylates/beheneth-25 methacrylate copolymer), Structure 2001® (acryla-tes/steareth-20 itaconate copolymer), Structure 3001® (acrylates/eteth-20 itaconate copolymer), Structure Plus® (Acrylates/Aminoacrylates C10-30 Alkyl PEG-20 Itaconate Copolymer), Carbopol® 1342, 1382, Ultrez 20, Ultrez 21 (Acrylates/C10-30 Alkyl Acrylates Crosspolymer), Synthalen W 2000® (Acrylates/Palmeth-25 Acrylates Copolymer) or the Soltex OPT (Acrylates/C12-22 Alkyl Methacrylate Copolymer) distributed by Rohme and Haas.

The homo- and copolymers of N-vinylpyrrolidone, vinylcaprolactam, vinyl-(C1-C6)alkyl-pyrrole, vinyl-oxazole, vinyl-thiazole, vinylpyrimidine, vinylimidazole can be named as suitable polymers based on vinyl monomers.

Furthermore, the copolymers octylacrylamide/acrylates/butylaminoethyl-methacrylate copolymer, as commercially marketed under the trade names AMPHOMER® or LOVOCRYL® 47 by NATIONAL STARCH, or the copolymers of acrylates/octylacrylamides marketed under the trade names DERMACRYL® LT and DERMACRYL® 79 by NATIONAL STARCH are particularly suitable.

Suitable olefin-based polymers include homopolymers and copolymers of ethylene, propylene, butene, isoprene and butadiene.

In another version, block copoylmers can be used as film-forming hydrophobic polymers, which comprise at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

Surprisingly, it turned out that particularly good dyeing's can be obtained with the anionic direct dyes, if the film-forming hydrophobic polymer also carries anionic charges.

In a further explicitly particularly preferred embodiment, an agent as contemplated herein contains (c) at least one anionic, film-forming, hydrophobic polymer.

An anionic polymer is a polymer comprising repeating units having at least one carboxylic acid group, one sulphonic acid group and/or their physiologically acceptable salts. In other words, an anionic polymer is made from monomers having at least one carboxylic acid group, a sulphonic acid group. In this context, the hydrophobic, film-forming copolymers of acrylic acid and the copolymers of methacrylic acid are particularly preferred. The polymers in this group contain the carboxylic acid groups, the sulphonic acid groups or their salts in an amount that ensures that the hydrophobic character of the whole polymer is maintained.

The film-forming hydrophobic polymer or polymers (c) as contemplated herein are preferably used in certain quantity ranges in the means as contemplated herein. In this context, it has proved to be particularly preferred for the solution of the task as contemplated herein if the agent—based on its total weight—contains one or more polymers in a total amount of from about 0.1 to about 25.0% by weight, preferably from about 0.2 to about 20.0% by weight, further preferably from about 0.5 to about 15.0% by weight and very particularly preferably from about 1.0 to about 7.0% by weight.

In a further preferred embodiment, an agent as contemplated herein contains—based on its total weight—one or more film-forming hydrophobic polymers (b) in a total amount of from about 0.1 to about 25.0% by weight, preferably from about 0.2 to about 20.0% by weight, more preferably from about 0.5 to about 15.0% by weight and very particularly preferably from about 1.0 to about 7.0% by weight.

Water Content of the Agents

The composition as contemplated herein contains the essential ingredients (a), (b) and (c) in a cosmetic carrier, preferably in an aqueous or water-containing cosmetic carrier.

Without being bound to this theory, it is assumed that the organic silicon compound (a), which comprises one or more hydroxyl groups or hydrolysable groups per molecule, is hydrolyzed and/or oligomerized in the presence of the water. The resulting hydrolysis products or oligomers have a particularly high affinity to the surface of the Keratin material. The direct dyes (b), especially the anionic direct dyes, together with the film-forming, hydrophobic polymer (c) can thus form a particularly stable and resistant film. In this context, it has proved to be particularly preferable if the agent—based on its total weight—has a water content of from about 15 to about 95% by weight, preferably from about 20 to about 95% by weight, more preferably from about 25 to about 95% by weight, still more preferably from about 30 to about 95% by weight and very preferably from about 45 to about 95% by weight.

In a further explicitly very particularly preferred form of execution, an agent as contemplated herein has—based on its total weight—a water content of from about 15 to about 95% by weight, preferably of from about 20 to about 95% by weight, more preferably of from about 25 to about 95% by weight, still more preferably of from about 30 to about 95% by weight and very particularly preferably of from about 45 to about 95% by weight.

Multi-Component Packaging Unit (Kit-of-Parts)

The agent of the first subject of the present disclosure described above is the coloring agent ready for use. Together with the organic silicon compound(s), it contains (a) a class of reactive compounds which can undergo hydrolysis and/or oligomerization in the presence of water as described above.

To increase storage stability, this agent is preferably provided to the user in the form of a multi-component packaging unit (kit-of-parts). Shortly before application on the keratinous material, the user can mix the different components of this packaging unit to produce the ready-to-use dye.

A second object of the present disclosure is a multi-component packaging unit (kit-of-parts) for dyeing keratinous material, in particular human hair, which separately includes a first container containing a cosmetic product (I) and
a second container containing a cosmetic product (II) and
a third container containing a cosmetic product (III),
where
the means (I) contains at least one organic silicon compound (a) as already disclosed in detail in the description of the first subject matter of the present disclosure,
the agent (II) contains water and
the agent (III) contains at least one direct dye (b) and at least one film-forming hydrophobic polymer (c), as already disclosed in detail in the description of the first subject matter of the present disclosure.

In a particularly preferred version, the ready-to-use dye is produced by mixing agents (I), (II) and (III). In this version, all three agents (I), (II) and (III) are applied simultaneously to the keratinous material.

For example, the user can first mix or shake the agent (I) containing the organic silicon compound(s) (a) with the water-containing agent (II). The user can then add agent (III) containing the direct dye(s) (b) and the film-forming hydrophobic polymer(s) (c) to the mixture of (I) and (II) and mix all three agents together.

In another particularly preferred version, it is also possible to apply agents (I), (II) and (III) successively on the keratinous material, so that the agents interact with each other only on the keratinous material.

For example, the user can first mix or shake the agent (I) containing the organic silicon compound(s) (a) with the water-containing agent (II). The user can now apply this mixture of (I) and (II) to the keratin materials—either directly after their production or after a short reaction time of from about 10 seconds to about 20 minutes. The user can then apply agent (III), which contains direct dye (b) and film-forming hydrophobic polymer (c), to the keratin material.

Agent (I) contains at least one organic silicon compound (a) as already disclosed in detail in the description of the first subject matter of the present disclosure. Thus the composition (I) contains at least one organic silicon compound (a) selected from silanes having one, two or three silicon atoms, the organic silicon compound further comprising one or more basic chemical functions and one or more hydroxyl groups or hydrolysable groups per molecule. With preference, agent (I) contains at least one organic silicon compound (a) of formula (I) and/or (II), where the radicals may represent the, preferred and particularly preferred substitutes. As organic silicon compound (a) the substances already mentioned can also be used.

To provide a formulation that is as stable as possible during storage, the agent (I) itself is preferably packaged with low or no water.

A multi-component packaging unit (kit-of-parts) as contemplated herein the agent (I)—based on the total weight of the agent (I)—contains a water content of less than about 10% by weight, preferably less than about 5% by weight, more preferably less than about 1% by weight, still more preferably less than about 0.1% by weight and very particularly preferably less than about 0.01% by weight.

Agent (II) contains water. A multi-component packaging unit (kit-of-parts) as contemplated herein the agent (II)—based on the total weight of the agent (II)—has a water content of from about 15 to about 100% by weight, preferably of from about 35 to about 100% by weight, more preferably of from about 55 to about 100% by weight, still more preferably of from about 65 to about 100% by weight and very particularly preferably of from about 75 to about 100% by weight.

Agent (III) contains at least one direct dye (b) and at least one film-forming hydrophobic polymer (c), as already disclosed in detail in the description of the first subject matter of the present disclosure.

In a particularly preferred form, the agent (III) contains the above-mentioned, the preferred and the particularly preferred direct dyes (b).

In a further preferred design, a multi-component packaging unit as contemplated herein the agent (III) contains—based on the total weight of the agent (III)—one or more direct-acting dyes (b) in a total amount of from about 0.01 to about 10.0% by weight, preferably from about 0.1 to about 8.0% by weight, more preferably from about 0.2 to about 6.0% by weight and very particularly preferably from about 0.5 to about 4.5% by weight.

In a particularly preferred form, the agent (III) contains the, the preferred and the particularly preferred film-forming hydrophobic polymers (c).

In a further preferred embodiment, a multi-component packaging unit as contemplated herein the agent (III) contains—based on the total weight of agent (III)—one or more film-forming hydrophobic polymers (b) in a total amount of from about 0.1 to about 25.0% by weight, preferably from about 0.2 to about 20.0% by weight, more preferably from about 0.5 to about 15.0% by weight and very particularly preferably from about 1.0 to about 7.0% by weight.

Agents (I) and (II) or agents (I), (II) and (III) can be mixed in different quantities. For example, the first container may contain from about 5 g to about 200 g of the agent (I). The second container can contain from about 5 g to about 200 g of the agent (II). The third container can contain from about 5 b to about 200 g of the agent (III).

Other Ingredients

The means described above, i.e. the ready-to-use employing the first subject matter of the present disclosure, and also means (I), (II) and (III) of the inventive kit of the second subject matter of the present disclosure, may also contain one or more optional ingredients.

The products may also contain one or more surfactants. The term surfactants refer to surface-active substances. A distinction is made between anionic surfactants including a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —$COO^{(-)}$— or —$SO_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —$SO_3H$ group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino propionates, aminoglycinate, imidazoliniumbetaines and sulfobetaines.

Particularly preferred ampholytic surfactants are N-cocoalkylaminopropionate, cocoacylaminoethylaminopropionate and $C_{12}$-$C_{18}$ acylsarcosine.

The products may also additionally contain at least one non-ionic surfactant. Suitable non-ionic surfactants are alkyl polyglycosides as well as alkylene oxide addition products to fatty alcohols and fatty acids with 2 to 30 mol ethylene oxide per mol fatty alcohol or fatty acid. Preparations with good properties are also obtained if they contain as non-ionic surfactants fatty acid esters of ethoxylated glycerol reacted with at least 2 mol ethylene oxide. The non-ionic surfactants are used in a total quantity of from about 0.1 to about 45% by weight, preferably from about 1 to about 30% by weight and very preferably from about 1 to about 15% by weight—based on the total weight of the respective agent.

In addition, the products may also contain at least one cationic surfactant. Cationic surfactants are surfactants, i.e. surface-active compounds, each with one or more positive charges. Cationic surfactants contain only positive charges. Usually these surfactants are composed of a hydrophobic part and a hydrophilic head group, the hydrophobic part usually including a hydrocarbon backbone (e.g. including one or two linear or branched alkyl chains) and the positive charge(s) being located in the hydrophilic head group. Examples of cationic surfactants are quaternary ammonium compounds which, as hydrophobic radicals, may carry one or two alkyl chains with a chain length of 8 to 28 C atoms, quaternary phosphonium salts substituted with one or more alkyl chains with a chain length of 8 to 28 C atoms or tertiary sulfonium salts.

Furthermore, the cationic charge can also be part of a heterocyclic ring (e.g. an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of from about 0.1 to about 45 wt. %, preferably from about 1 to about 30 wt. % and most preferably from about 1 to about 15 wt. %—based on the total weight of the respective agent.

Furthermore, the means as contemplated herein may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

The anionic surfactants are used in a total quantity of from about 0.1 to about 45 wt. %, preferably from about 1 to about 30 wt. % and most preferably from about 1 to about 15 wt. %—based on the total weight of the respective agent.

They may also contain other active substances, auxiliaries and additives, such as solvents, fatty components such as $C_8$-$C_{30}$ fatty alcohols, $C_8$-$C_{30}$ fatty acid triglycerides, $C_8$-$C_{30}$ fatty acid monoglycerides, $C_8$-$C_{30}$ fatty acid diglycerides and/or hydrocarbons; structural agents such as glucose, maleic acid and lactic acid; hair conditioning compounds such as phospholipids, for example lecithin and cephalins; perfume oils, dimethylisosorbide and cyclodextrins; fiber structure-improving active substances, in particular mono-, di- and oligosaccharides such as glucose, galactose, fructose, fructose and lactose; dyes for coloring the composition; anti-dandruff active substances such as Piroctone Olamine, Zinc Omadine and Climbazol; amino acids and oligopeptides; protein hydrolysates on animal and/or vegetable basis, as well as in the form of their fatty acid condensation products or optionally anionic or cationically modified derivatives; vegetable oils; sunscreens and UV-blockers; active ingredients such as panthenol, pantothenic acid, pantolactone, allantoin, pyrrolidinonecarboxylic acids and their salts, and bisabolol; polyphenols, in particular hydroxycinnamic acids, 6,7-dihydroxycumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; and blowing agents such as propane-butane mixtures, $N_2O$, dimethyl ether, $CO_2$ and air.

The selection of these other substances will be made by the specialist according to the desired properties of the agents. About other optional components and the quantities of these components used, explicit reference is made to the relevant manuals known to the specialist. The additional active ingredients and auxiliary substances are preferably used in the preparations as contemplated herein in quantities of from about 0.0001 to about 25 wt. % each, from about 0.0005 to about 15 wt. %, based on the total weight of the respective agent.

Process for Dyeing Keratin Materials

The agents described above—both the ready-to-use agent of the first subject-matter of the present disclosure and the agents of the multi-component packaging unit of the second subject-matter of the present disclosure—are used in processes for dyeing keratinous materials, in particular for dyeing human hair.

A third subject of the present disclosure is a process for dyeing keratinous material, in particular human hair, comprising the following steps in the order indicated:

(1) Application of a pre-treatment agent (V) to the keratinous material, the pre-treatment agent (V) containing, in an aqueous cosmetic carrier, at least one organic silicon compound (a) as already disclosed in detail in the description of the first subject-matter of the present disclosure, (2) Application of a coloring agent (F) to the keratinous material, the coloring agent comprising at least one direct dye (b) and at least one film-forming hydrophobic polymer (c), as already disclosed in detail in the description of the first subject-matter of the present disclosure.

In other words, a third subject-matter of the present disclosure is a process for coloring keratinous material, in particular human hair, comprising the following steps in the order indicated:

(1) application of a pretreatment agent (V) to the keratinous material, the said pretreatment agent (V) comprising, in a water-containing cosmetic carrier, at least one organic silicon compound (a) chosen from silanes containing one, two or three silicon atoms, the said organic silicon compound also comprising one or more basic chemical functions and one or more hydroxyl or hydrolysable groups per molecule, and (2) Application of a coloring agent (F) to the keratinous material, the coloring agent comprising at least one direct dye (b) and at least one film-forming hydrophobic polymer (c).

In other words, a third subject-matter of the present disclosure is a process for coloring keratinous material, in particular human hair, comprising the following steps in the order indicated:

(1) application of a pretreatment agent (V) to the keratinous material, the said pretreatment agent (V) comprising, in a water-containing cosmetic carrier, at least one organic silicon compound (a) chosen from silanes containing one, two or three silicon atoms, the said organic silicon compound also comprising one or more basic chemical functions and one or more hydroxyl or hydrolysable groups per molecule, and (2) Application of a coloring agent (F) to the keratinous material, the coloring agent comprising at least one anionic direct dye (b) and at least one anionic film-forming hydrophobic polymer (c).

In the process as contemplated herein, the keratin materials, in particular human hair, are first treated with a pretreatment agent (V). Subsequently, the actual dye (F)—which contains the film-forming hydrophobic polymer and the direct dye(s)—is applied to the keratin materials.

Preferably, the pretreatment agent (V) itself does not contain any dyes or coloring compounds. The pre-treatment agent (V) is exemplified by its content of at least one reactive organic silicon compound (a). Without being limited to this theory, it is believed that the organic silicon compounds (a) functionalize the hair surface as soon as they meet it. In this way a first, still uncolored film or layer is formed. In the second step of the process, a coloring agent (F) is now applied to the hair. During the application of the dye (F) on the keratin materials, a film is also formed on the—now already functionalized—hair surface, whereby the direct dyes are now embedded in the film and thus deposited on the hair. The film produced "in situ" in this way, in which the direct-drawing dyes are embedded, is exemplified by outstanding wash fastness and a homogeneous color result. The colors are shiny, and the feel of the dyed keratin materials is smooth and pleasant.

The pre-treatment agent (V) represents the pre-treatment agent (V) ready for use. In particular, the pre-treatment agent (V) is a mixture of agents (I) and (II) of the multi-component packaging unit as contemplated herein. The pretreatment agent (V) thus contains at least one organic silicon compound (a) selected from silanes having one, two or three silicon atoms, the organic silicon compound further comprising one or more basic chemical functions and one or more hydroxyl groups or hydrolysable groups per molecule. Preferably the pretreatment agent (V) contains at least one organic silicon compound (a) of formula (I) and/or (II) described above, whereby the residues may stand for the already mentioned, the preferred and the particularly preferred substituents.

Furthermore, the pre-treatment agent (V) contains water, whereby the water preferably comes from the agent (II) of the kit-of-parts as contemplated herein.

In a particularly preferred embodiment, a process as contemplated herein is exemplified in that the pre-treatment agent (V) is prepared before application to the keratinous material by mixing a first agent (I) and a second agent (II), wherein the means (I) contains at least one organic silicon compound (a) as disclosed in detail in the description of the first and second subject matter of the present disclosure, and the agent (II) contains water.

It is preferred if the pre-treatment agent (V)—based on the total weight of the pre-treatment agent (V)—has a water content of from about 15 to about 95% by weight, preferably of from about 20 to about 95% by weight, more preferably of from about 25 to about 95% by weight, still more preferably of from about 30 to about 95% by weight and very particularly preferably of from about 45 to about 95% by weight.

In a further very particularly preferred form of execution, a process as contemplated herein is exemplified in that the pre-treatment agent (V)—based on the total weight of the pre-treatment agent—has a water content of from about 15 to about 95% by weight, preferably of from about 20 to about 95% by weight, more preferably of from about 25 to about 95% by weight, still more preferably of from about 30 to about 95% by weight and very particularly preferably of from about 45 to about 95% by weight.

Especially resistant dyeing's could be obtained by using an alkaline pre-treatment agent (V). Preferably, the pretreatment agent (V) has a pH value of from about 7.0 to about 11.5, preferably from about 7.5 to about 11.0 and particularly preferably from about 8.0 to about 10.5.

In a further particularly preferred form of execution, a process as contemplated herein is exemplified in that the pretreatment agent (V) has a pH value of from about 7.0 to about 11.5, preferably of from about 7.5 to about 11.0 and particularly preferably of from about 8.0 to about 10.5.

To adjust these alkaline pH values, the pre-treatment agent (V) preferably contains at least one alkalizing agent, which is added in a quantity that ensures the adjustment of the optimal pH value for the respective hair treatment. The pH values for the purposes of the present disclosure are pH values measured at a temperature of about 22° C.

Depending on the choice of the desired pH value and depending on the presence of other components in the agent as contemplated herein, such as acidic or basic salts or buffer components, the amount of alkalizing agent added can vary, usually requiring amounts of from about 0.01 to about 15% by weight.

As alkalizing agent, the pre-treatment agent (V) can contain for example ammonia, alkanolamines and/or basic amino acids.

The alkanolamines which can be used in the pretreatment agent (V) as contemplated herein are preferably selected from primary amines with a $C_2$-$C_6$ alkyl base body which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment the agent as contemplated herein contains an alkanolamine selected from 2-aminoethan-1-ol and/or 2-amino-2-methylpropan-1-ol as alkalizing agent.

For the purposes of the present disclosure, a basic amino acid is an organic compound which contains in its structure at least one protonatable amino group and at least one —COOH or —$SO_3H$ group. Preferred amino acids are aminocarboxylic acids, especially α-(alpha)-aminocarboxylic acids and ω-aminocarboxylic acids, whereby α-aminocarboxylic acids are particularly preferred.

As contemplated herein, basic amino acids are those amino acids which have an isoelectric point pI of greater than about 7.0.

Basic α-aminocarboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine, and histidine, especially preferably arginine and lysine. In another particularly preferred embodiment, an agent as contemplated herein the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1- ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

In a further particularly preferred embodiment, a process as contemplated herein the pretreatment agent (V) contains at least one alkalizing agent which is preferably selected from the group including ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol, arginine, lysine, ornithine, Histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Apart from the alkalizing agents described above, experts are familiar with common acidifying agents for fine adjustment of the pH value. As contemplated herein, preferred acidifiers are pleasure acids, such as citric acid, acetic acid, malic acid, or tartaric acid, as well as diluted mineral acids.

Following the application of the pre-treatment agent (V), the colorant (F) is applied to the keratin materials. The colorant (F) is the ready-to-use colorant (F).

The coloring agent (F) contains the direct dye(s) (b) and the hydrophobic film-forming polymer(s) (c) in a cosmetic carrier, preferably in a water-containing cosmetic carrier.

In a further very particularly preferred embodiment, a process as contemplated herein the colorant (F)—based on the total weight of the colorant (F)—has a water content of from about 15 to about 95% by weight, preferably of from about 20 to about 95% by weight, more preferably of from about 25 to about 95% by weight, still more preferably of from about 30 to about 95% by weight and very particularly preferably of from about 45 to about 95% by weight.

To produce particularly wash-fast dyeing's, it has also proved to be particularly preferred if the dye (F) is also alkaline and has a pH value of from about 7.0 to about 11.5, preferably from about 7.5 to about 11.0 and particularly preferably from about 8.0 to about 10.5.

In a further particularly preferred embodiment, a process as contemplated herein the colorant (F) has a pH value of from about 7.0 to about 11.5, preferably of from about 7.5 to about 11.0 and particularly preferably of from about 8.0 to about 10.5.

To adjust this alkaline pH, the coloring agent (F) also contains preferably at least one alkalizing agent, added in a quantity that ensures the adjustment of the optimal pH value for the hair treatment in question. The pH values for the purposes of the present disclosure are pH values measured at a temperature of about 22° C.

The coloring agent (F) may contain at least one alkalizing agent from the group mentioned above. In particular, the coloring agent (F) contains at least one alkalizing agent preferably selected from the group including ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-Amino-2-methylpropan-1-ol, 1-amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate In a further particularly preferred embodiment, a process as contemplated herein the colorant (F) contains at least one alkalizing agent which is preferably selected from the group including ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol, arginine, lysine, ornithine, Histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Procedural Steps

The technical application properties of the resulting dyeing can be further improved by choosing the optimum process conditions.

In the context of a further form of execution, a procedure comprising the following steps in the order indicated is particularly preferred (1) Application of the pre-treatment agent (V) on the keratinous material, (2) Allow the pre-treatment agent (V) to act for a period of from about 10 seconds to about 10 minutes, preferably from about 10 seconds to about 5 minutes, (3) if necessary, rinse out the pre-treatment agent (V), (4) Application of the coloring agent (F) on the keratinous material, (5) leave the dye (F) to act for a period of from about 30 seconds to about 30 minutes, preferably from about 30 seconds to about 10 minutes, and (6) application of a conditioner if necessary and (7) Rinse out the keratinous material.

In a first step (1), the pre-treatment agent (V) is applied to the keratin materials, especially human hair.

After application, the pre-treatment agent (V) can act on the keratin materials. In this context, application times from about 10 seconds to about 10 minutes, preferably from about 20 seconds to about 5 minutes and especially preferably from about 30 seconds to about 2 minutes on the hair have proven to be particularly beneficial.

In a further preferred embodiment, a process as contemplated herein is exemplified by (2) Allow the pre-treatment agent (V) to act on the keratin materials for a period of from about 10 seconds to about 10 minutes, preferably from about 10 seconds to about 5 minutes and most preferably from about 30 seconds to about 2 minutes.

In a preferred embodiment of the process as contemplated herein, the pretreatment agent (V) can now be rinsed from the keratin materials before the coloring agent (F) is applied to the hair in the following step.

In a further embodiment, a process comprising the following steps in the order given is particularly preferred (1) Application of the pre-treatment agent (V) on the keratinous material, (2) Allow the pre-treatment agent (V) to act for a period of from about 10 seconds to about 10 minutes, preferably from about 10 seconds to about 5 minutes, (3) Rinse out the pretreatment agent (V),
(4) Application of the coloring agent (F) on the keratinous material,
(5) leave the dye (F) to act for a period of from about 30 seconds to about 30 minutes, preferably from about 30 seconds to about 10 minutes, and
(6) application of a conditioner if necessary and
(7) Rinse out the keratinous material.

Dyeing's with also good wash fastness properties were obtained when the dye (F) was applied to the keratin materials which were still exposed to the pretreatment agent (V).

In a further embodiment, a process comprising the following steps in the order given is particularly preferred
(1) Application of the pre-treatment agent (V) on the keratinous material,
(2) Allow the pre-treatment agent (V) to act for a period of from about 10 seconds to about 10 minutes, preferably from about 10 seconds to about 5 minutes,
(3) no rinsing of the pretreatment agent (V),
(4) Application of the coloring agent (F) on the keratinous material,
(5) leave the dye (F) to act for a period of from about 30 seconds to about 30 minutes, preferably from about 30 seconds to about 10 minutes, and
(6) application of a conditioner if necessary and
(7) Rinse out the keratinous material.

In step (4) the dye (F) is now applied to the keratin materials. After application, let the colorant (F) act on the hair.

The process as contemplated herein allows the production of dyeing's with particularly good intensity and wash fastness, even with a short reaction time of the dye (F). Application times from about 10 seconds to about 10 minutes, preferably from about 20 seconds to about 5 minutes and most preferably from about 30 seconds to about 3 minutes on the hair have proven to be particularly beneficial.

In a further preferred embodiment, a process as contemplated herein is exemplified by
(5) Allow the dye (F) to act on the hair for a period of from about 10 seconds to about 10 minutes, preferably from about 20 seconds to about 5 minutes and most preferably from about 30 seconds to about 3 minutes.

In a further embodiment, a process comprising the following steps in the order given is particularly preferred
(1) Application of the pre-treatment agent (V) on the keratinous material,
(2) Allow the pre-treatment agent (V) to act for a period of from about 10 seconds to about 10 minutes, preferably from about 10 seconds to about 5 minutes,
(3) Rinse out the pretreatment agent (V),
(4) Application of the coloring agent (F) on the keratinous material,
(5) Allow the dye (F) to act on the hair for a period of from about 10 seconds to about 10 minutes, preferably from about 20 seconds to about 5 minutes and most preferably from about 30 seconds to about 3 minutes, and
(6) application of a conditioner if necessary and
(7) Rinse out the keratinous material.

After the dye (F) has taken effect, a conditioner can now optionally be applied.

In a further embodiment, a process comprising the following steps in the order given is particularly preferred
(1) Application of the pre-treatment agent (V) on the keratinous material,
(2) Allow the pre-treatment agent (V) to act for a period of from about 10 seconds to about 10 minutes, preferably from about 10 seconds to about 5 minutes,
(3) Rinse out the pretreatment agent (V),
(4) Application of the coloring agent (F) on the keratinous material,
(5) Allow the dye (F) to act on the hair for a period of from about 10 seconds to about 10 minutes, preferably from about 20 seconds to about 5 minutes and most preferably from about 30 seconds to about 3 minutes, and
(6) Application of a conditioner and
(7) Rinse out the keratinous material.

Preferably, the conditioner contains at least one cationic and/or non-ionic surfactant.

Surprisingly, it turned out that using the conditioner—especially if it contains at least one cationic surfactant—may further improve the fastness of the dyeing's obtained and further intensify the color result.

In a further preferred embodiment, a process as contemplated herein conditioner contains at least one cationic and/or non-ionic surfactant.

In another particularly preferred version, a process as contemplated herein the conditioner contains at least one cationic surfactant.

To obtain a coloring that is as homogeneous and resistant as possible, it has been found to be particularly preferable if there is a period of maximum about 48 hours, preferably maximum about 24 hours, more preferably maximum about 12 hours and most preferably maximum about 6 hours between the application of the pre-treatment agent (V) and the application of the coloring agent (F).

In a further preferred embodiment, a process as contemplated herein the pretreatment agent (V) and the coloring agent (F) are applied to the hair within a period of at most about 48 hours, preferably at most about 24 hours, more preferably at most about 12 hours and most preferably at most 6 hours.

About the other preferred embodiments of the multi-component packaging unit and the process as contemplated herein, what is said about the means as contemplated herein applies mutatis mutandis.

Examples

1. Formulations

The following formulations have been produced (unless otherwise indicated, all figures are in % by weight)
Pretreatment Agent (V)

| Agent (I) | (I) |
|---|---|
| (3-Aminopropyl)triethoxysilan | 0.3 g |

| Agent (II) | (II) |
|---|---|
| Sodium hydroxide | ad pH 10.0 |
| Water | ad 100 wt.-% |

By mixing about 0.3 g of agent (I) and about 100 g of agent (II), the pre-treatment agent (V) was prepared ready for use. This involved shaking agents (I) and (II) together for about 3 minutes. Then the pre-treatment agent (V) was left to stand for about 5 minutes. The pH value of the ready-to-use pre-treatment agent (V) was about 10.

| Coloring agent (F) | | | | |
|---|---|---|---|---|
| Agent (III) | V F1 | E F2 | V F3 | E F4 |
| Colorona Bronze (Merck, Mica, CI77491, Iron oxides, CI77019) | 1.0 | — | — | — |
| Acid Yellow 1 | — | 1.0 | — | — |
| Unipure Red LC 3071 (Sensient, Aluminum hydroxide, CI 15850) | — | — | 1.0 | — |
| Acid Red 33 | — | — | — | 1.0 |
| Dermacryl 79 (Akzo Nobel, Acrylates/Octylacrylamide Copolymer, CAS-No. 129702-02-9) | 9.0 | 9.0 | — | — |
| Aculyn 22 (Rohm & Haas, ACRYLATES/STEARETH-20 METHACRYLATE COPOLYMER | — | — | 5.0 | 5.0 |
| Ammonia (25% aqueous solution) | ad pH 10 | ad pH 10 | ad pH 10 | ad pH 10 |
| Water | ad 100 | ad 100 | ad 100 | ad 100 |

| | V F5 | E F6 | V F7 | E F8 |
|---|---|---|---|---|
| Covapearl. Fire Red 333 AS (Sensient, Fire red pigment, Mica, CI 77491 (Iron oxides, Triethoxycaprilylsilane) | 1.5 | — | — | — |
| Acid Red 92 | — | 1.5 | — | — |
| Timiron Splendid Copper (117478) (Mercke, Titanium dioxide, Mica Silica, CI 77891) | — | — | 0.5 | — |
| Acid Orange 7 | — | — | — | 0.5 |
| Soltex OPT (Rohm & Haas, Acrylates/C12-22 Alkyl methacrylate Copolymer) | 6.0 | 6.0 | — | — |
| Aculyn 28 (Rohm & Haas, ACRYLATES/BEHENETH-25 METHACRYLATE COPOLYMER) | — | — | 6.0 | 6.0 |
| Ethanolamine | ad pH 10 | ad pH 10 | ad pH 10 | ad pH 10 |
| Water | ad 100 | ad 100 | ad 100 | ad 100 |

V = Comparison
E = according to present disclosure

| Conditioner (C) | |
|---|---|
| Cetearyl alcohol | 5.0 |
| Ceteareth-20 | 0.3 |
| Isopropyl myristate | 0.8 |
| Stearamidopropyldimethylamine | 0.4 |
| Quaternium-87 | 3.0 |
| Propylene glycol | 1.0 |
| Citric acid | 0.95 |
| Glyceryl stearate | 0.3 |
| Water | Ad 100 |

2. Application

One strand of hair at a time (Kerling, Euronature hair white) was dipped into the pre-treatment agent (V) and left there for about 1 minute. Afterwards, excess pre-treatment agent was stripped from each strand of hair. Each strand of hair was washed out with water. Excess water was scraped off each strand of hair.

The strands of hair were then each dipped in one of the dyes (F) and left there for about 1 minute.

The strands of hair were then each wetted with a small amount of the conditioner and then rinsed with water and dried. Afterwards the strands were visually evaluated.

| Specimen | 1 | 2 | 3 | 4 |
|---|---|---|---|---|
| Pretreatment agent (V) | (V) | (V) | (V) | (V) |
| Coloring agent (F) | (F1) Colorona Bronze | (F2) Acid Yellow 1 | (F3) Unipure Red LC 3071 | (F4) Acid Red 33 |
| Conditioner (C) | (C) | (C) | (C) | (C) |
| Coloring | bronze yellow | golden yellow | red | red |
| Color Intensity | +++ | +++ | +++ | +++ |
| Hair feeling | rough/blunt | smooth/soft | rough/blunt | smooth/soft |
| Combability | + | +++ | + | +++ |

| Specimen | 5 | 6 | 7 | 8 |
|---|---|---|---|---|
| Pretreatment agent (V) | (V) | (V) | (V) | (V) |
| Coloring agent (F) | (F5) Covapearl. Fire Red 333 AS | (F6) Acid Red 92 | (F7) Timiron Splendid Copper | (F8) Acid Orange 7 |
| Conditioner (C) | (C) | (C) | (C) | (C) |
| Coloring | red | red | orange-copper | orange-copper |
| Color Intensity | +++ | +++ | +++ | +++ |
| Hair feeling | rough/blunt | smooth/soft | rough/blunt | smooth/soft |
| Combability | + | +++ | + | +++ |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A composition for dyeing keratinous material comprising, in a cosmetic carrier, (a) at least one organic silicon compound selected from silanes comprising formula (I) and/or (II),

$$R_1R_2N\text{-}L\text{-}Si(OR_3)_a(R_4)_b \qquad (I),$$

where
$R_1$ and $R_2$ independently represent a hydrogen atom or a $C_1$-$C_6$ alkyl group,
L is a linear or branched divalent $C_1$-$C_{20}$ alkylene group,
$R_3$ represents a hydrogen atom or a $C_1$-$C_6$ alkyl group,
$R_4$ represents a $C_1$-$C_6$ alkyl group,
a, stands for an integer from 1 to 3, and
b stands for the integer 3-a,

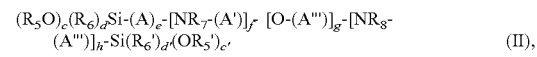

$$(R_5O)_c(R_6)_d Si\text{-}(A)_e\text{-}[NR_7\text{-}(A')]_f\text{-}[O\text{-}(A''')]_g\text{-}[NR_8\text{-}(A''')]_h\text{-}Si(R_6')_{d'}(OR_5')_{c'} \qquad (II),$$

where
R_5, R_5', and R_5'' independently represent a hydrogen atom or a $C_1$-$C_6$ alkyl group,
R_6, R_6', and R_6'' independently represent a $C_1$-$C_6$ alkyl group,
A, A', A'', A''', and A'''' independently of one another represent a linear or branched divalent $C_1$-$C_{20}$ alkylene group, and
R_7 and R_8 independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III)

$$—(A'''')-Si(R_6'')_{d''}(OR_5'')_{c''} \quad (III)$$

wherein
c, stands for an integer from 1 to 3,
d stands for the integer 3-c,
c' stands for an integer from 1 to 3,
d' stands for the integer 3-c',
c'' stands for an integer from 1 to 3,
d'' stands for the integer 3-c'',
e stands for 0 or 1,
f stands for 0 or 1,
g stands for 0 or 1,
h stands for 0 or 1,
provided that at least one of e, f, g, and h is different from 0,
(b) at least one anionic direct dye in a total amount of from about 0.01 to about 10.0% by weight of the total composition, wherein the direct dye is selected from the group of nitrophenylenediamines, nitroaminophenols, azo dyes, anthraquinone dyes, triarylmethane dyes, xanthene dyes, rhodamine dyes, oxazine dyes and/or indophenol dyes, wherein the dyes from the aforementioned group each have at least one carboxylic acid group (—COOH), a sodium carboxylate group (—COONa), a potassium carboxylate group (—COOK), a sulphonic acid group (—SO_3H), a sodium sulphonate group (—SO_3Na) and/or a potassium sulphonate group (—SO_3K), and wherein the anionic direct dye have a solubility in water (about 760 mmHg) at about 25° C. of more than about 0.5 g/L; and
(c) at least one film-forming hydrophobic polymer selected from copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters, polyamides and combinations thereof, wherein the at least one film-forming hydrophobic polymer has a molecular weight of no more than $10^7$ grams/mole (g/mol) and is added in an amount of from about 0.1 to about 25.0% by weight of the total composition a), b) and c).

2. The composition according to claim 1, wherein the composition comprises (a) at least one organic silicon compound of the formula (I),
where
R_1 and R_2 both represent a hydrogen atom, and
L represents a linear, divalent $C_1$-$C_6$-alkylene group.

3. The composition according to claim 1, wherein the composition comprises (a) at least one organic silicon compound of the formula (I),
where
R_3, R_4 independently of one another represent a methyl group or an ethyl group,
a stands for the number 3, and
b stands for the number 0.

4. The composition according to claim 1, wherein the composition comprises (a) at least one organic silicon compound of the formula (I) selected from the group of
(3-Aminopropyl)triethoxysilan
(3-Aminopropyl)trimethoxysilane
1-(3-Aminopropyl)silantriol
(2-Aminoethyl)triethoxysilan
(2-Aminoethyl)trimethoxysilane
1-(2-Aminoethyl)silantriol
(3-Dimethylaminopropyl)triethoxysilan
(3-Dimethylaminopropyl)trimethoxysilane
1-(3-Dimethylaminopropyl)silantriol
(2-Dimethylaminoethyl)triethoxysilan
(2-Dimethylaminoethyl)trimethoxysilane and/or
1-(2-Dimethylaminoethyl)silantriol.

5. The composition according to claim 1, wherein the composition comprises (a) at least one organic silicon compound of formula (II),
where
R_5 and R_5' independently represent a methyl group or an ethyl group,
c and c' both stand for the number 3, and
d and d' both stand for the number 0.

6. The composition according to claim 1, wherein the composition comprises (a) at least one organic silicon compound of formula (II),
where
e and f both stand for the number 1,
g and h both stand for the number 0,
A and A' independently represent a linear, divalent $C_1$-$C_6$ alkylene group, and
R7 represents a hydrogen atom, a methyl group, a 2-hydroxyethyl group, a 2-alkenyl group, a 2-aminoethyl group or a group of formula (III).

7. The composition according to claim 1, wherein the composition comprises (a) at least one organic silicon compound of the formula (II) selected from the group of
3-(Trimethoxysilyl)-N-[3-(trimethoxysilyl)propyl]-1-propanamine
3-(Triethoxysilyl)-N-[3-(triethoxysilyl)propyl]-1-propanamine
N-Methyl-3-(trimethoxysilyl)-N-[3-(trimethoxysilyl)propyl]-1-propanamine
N-Methyl-3-(triethoxysilyl)-N-[3-(triethoxysilyl)propyl]-1-propanamine
2-[Bis[3-(trimethoxysilyl)propyl]amino]-ethanol
2-[Bis[3-(triethoxysilyl)propyl]amino]ethanol
3-(Trimethoxysilyl)-N,N-bis[3-(trimethoxysilyl)propyl]-1-propanamine
3-(Triethoxysilyl)-N,N-bis[3-(triethoxysilyl)propyl]-1-propanamine
N1,N1-Bis[3-(trimethoxysilyl)propyl]-1,2-ethanediamine,
N1,N1-Bis[3-(triethoxysilyl)propyl]-1,2-ethanediamine,
N,N-Bis[3-(trimethoxysilyl)propyl]-2-propen-1-amine and/or
N,N-Bis[3-(triethoxysilyl)propyl]-2-propen-1-amine.

8. The composition according to claim 1, wherein the composition further comprises in (b) at least one anionic direct dye selected from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

9. The composition according to claim 1, wherein the composition has—based on its total weight—a water content of from about 15 to about 95% by weight.

10. A multicomponent packaging unit (kit-of-parts) for dyeing keratinous material comprising:
a first container comprising a cosmetic product (I),
a second container comprising a cosmetic product (II), and
a third container comprising a cosmetic product (III), wherein
the cosmetic product (I) comprises at least one organic silicon compound (a) as defined in claim 1,
the cosmetic product (II) comprises water, and
the cosmetic product (III) comprises at least one direct dye (b) and at least one film-forming hydrophobic polymer (c) as defined in claim 1.

11. A method for dyeing keratinous material comprising the following steps in the order indicated:

(1) application of a pretreatment agent (V) to the keratinous material, the pretreatment agent (V) comprising, in a water-containing cosmetic carrier, at least one organic silicon compound (a) as defined in claim 1, wherein the pretreatment agent (V) has a pH of from about 7 to about 11.5, (2) allowing the pre-treatment agent (V) to act on the keratinous material for a period of from about 10 seconds to about 10 minutes (3) rinsing the pretreatment agent (V) from the keratinous material;

(4) application of a coloring agent (F) to the keratinous material, the coloring agent comprising at least one direct dye (b) and at least one film-forming hydrophobic polymer (c) as defined in claim 1;

(5) optionally applying a conditioner to the keratinous material; and (6) rinsing the coloring agent (F) and optional conditioner from the keratinous material.

12. The method according to claim 11, wherein the pre-treatment agent (V) is prepared before application on the keratinous material by mixing a first agent (I) and a second agent (II), wherein
the first agent (I) comprises at least one organic silicon compound (a) as defined in claim 1, and
the second agent (II) comprises water.

13. The method according to claim 11, wherein the pre-treatment agent (V)—based on the total weight of the pre-treatment agent—has a water content of from about 15 to about 95% by weight.

* * * * *